United States Patent
Rousseau et al.

(10) Patent No.: US 9,144,511 B2
(45) Date of Patent: Sep. 29, 2015

(54) METHODS AND DEVICES FOR TREATMENT OF OBSTRUCTIVE SLEEP APNEA

(71) Applicant: ETHICON, INC., Somerville, NJ (US)

(72) Inventors: Robert A. Rousseau, Ottsville, PA (US); Kevin S. Weadock, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 355 days.

(21) Appl. No.: 13/784,077

(22) Filed: Mar. 4, 2013

(65) Prior Publication Data
US 2013/0174857 A1    Jul. 11, 2013

Related U.S. Application Data

(63) Continuation of application No. 12/228,681, filed on Aug. 14, 2008, now Pat. No. 8,413,661.

(51) Int. Cl.
A61F 5/56    (2006.01)

(52) U.S. Cl.
CPC .. *A61F 5/56* (2013.01); *A61F 5/566* (2013.01)

(58) Field of Classification Search
CPC .......................................................... A61F 5/56
USPC .................. 128/846, 848, 859–862; 602/902; 623/9, 11.11, 14.11
See application file for complete search history.

(56) References Cited

U.S. PATENT DOCUMENTS

| | | |
|---|---|---|
| 3,123,077 A | 3/1964 | Alcamo |
| 3,378,010 A | 4/1968 | Codling et al. |
| 4,024,855 A | 5/1977 | Bucalo |
| 4,069,825 A | 1/1978 | Akiyama |
| 4,290,763 A | 9/1981 | Hurst |
| 4,523,584 A | 6/1985 | Lynch |
| 4,557,264 A | 12/1985 | Hinsch |
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |
| 5,067,485 A | 11/1991 | Cowen |

(Continued)

FOREIGN PATENT DOCUMENTS

| | | |
|---|---|---|
| CN | 2465680 | 12/2001 |
| CN | 201029957 Y | 3/2008 |

(Continued)

OTHER PUBLICATIONS

Cole et al., "Snoring: A Review and a Reassessment", J. of Otolaryngology, vol. 24, No. 5 pp. 303-306 (1995).

(Continued)

*Primary Examiner* — Victoria J Hicks
*Assistant Examiner* — Tarla Patel

(57) ABSTRACT

A pharyngeal retractor device and implantation methods are provided for use in the treatment of obstructive sleep apnea. The device includes a retracting element and a tissue engaging element that promotes tissue ingrowth around or onto the retracting element. The device is implanted in tissue space beneath the pharyngeal wall to alter the shape of the wall. The device may be implanted through the oral cavity alone or by using a trocar or a hand-held delivery system to deliver the device through the pharyngeal wall. Alternatively, the device may be implanted using an open, direct visualization approach from the side of a patient's neck.

24 Claims, 12 Drawing Sheets

(56) References Cited

U.S. PATENT DOCUMENTS

| | | | |
|---|---|---|---|
| 5,123,913 A | 6/1992 | Wilk et al. |
| 5,192,271 A | 3/1993 | Kalb et al. |
| 5,192,274 A | 3/1993 | Bierman |
| 5,269,783 A | 12/1993 | Sander |
| 5,284,161 A | 2/1994 | Karell |
| 5,311,028 A | 5/1994 | Glavish |
| 5,393,984 A | 2/1995 | Glavish |
| 5,483,077 A | 1/1996 | Glavish |
| 5,484,444 A | 1/1996 | Braunschweiler et al. |
| 5,609,559 A | 3/1997 | Weitzner |
| 5,683,417 A | 11/1997 | Cooper |
| 5,704,895 A | 1/1998 | Scott et al. |
| 5,792,067 A | 8/1998 | Karell |
| 5,843,077 A | 12/1998 | Edwards |
| 5,931,855 A | 8/1999 | Buncke |
| 6,161,541 A | 12/2000 | Woodson |
| 6,190,401 B1 | 2/2001 | Green et al. |
| 6,241,747 B1 | 6/2001 | Ruff |
| 6,250,307 B1 | 6/2001 | Conrad et al. |
| 6,348,156 B1 | 2/2002 | Vishnoi et al. |
| 6,408,851 B1 | 6/2002 | Karell |
| 6,431,174 B1 | 8/2002 | Knudson et al. |
| 6,432,437 B1 | 8/2002 | Hubbard |
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 | 1/2006 | Jamiolkowski et al. |
| 7,017,582 B2 | 3/2006 | Metzger et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,261,702 B1 | 8/2007 | Alexandre et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,850,894 B2 | 12/2010 | Lindh, Sr. et al. |
| 7,857,829 B2 | 12/2010 | Kaplan et al. |
| 7,888,119 B2 | 2/2011 | Sugaya et al. |
| 8,142,422 B2 | 3/2012 | Makower et al. |
| 8,307,831 B2 | 11/2012 | Rousseau |
| 8,413,661 B2 | 4/2013 | Rousseau et al. |
| 8,800,567 B2 | 8/2014 | Weadock et al. |
| 2001/0037133 A1 | 11/2001 | Knudson et al. |
| 2002/0144685 A1 | 10/2002 | Ivanovich et al. |
| 2003/0004579 A1 | 1/2003 | Rousseau et al. |
| 2003/0034312 A1 | 2/2003 | Unger et al. |
| 2003/0149445 A1 | 8/2003 | Knudson et al. |
| 2003/0149447 A1 | 8/2003 | Morency et al. |
| 2003/0149488 A1 | 8/2003 | Metzger et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0044366 A1 | 3/2004 | Bonutti et al. |
| 2004/0102796 A1 | 5/2004 | Hill et al. |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0153127 A1 | 8/2004 | Gordon et al. |
| 2005/0038472 A1 | 2/2005 | Furst |
| 2005/0082452 A1 | 4/2005 | Kirby |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0126563 A1 | 6/2005 | van de Burg et al. |
| 2005/0159637 A9 | 7/2005 | Nelson et al. |
| 2005/0165352 A1 | 7/2005 | Henry et al. |
| 2005/0199248 A1 | 9/2005 | Pflueger et al. |
| 2005/0203576 A1 | 9/2005 | Sulamanidze et al. |
| 2005/0251255 A1 | 11/2005 | Metzger et al. |
| 2005/0267321 A1 | 12/2005 | Shadduck |
| 2005/0267531 A1 | 12/2005 | Ruff et al. |
| 2005/0267532 A1 | 12/2005 | Wu |
| 2005/0267571 A1 | 12/2005 | Spence et al. |
| 2005/0268919 A1 | 12/2005 | Conrad et al. |
| 2005/0279365 A1 | 12/2005 | Armijo et al. |
| 2006/0005843 A9 | 1/2006 | Nelson et al. |
| 2006/0079935 A1 | 4/2006 | Kolster |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1 | 9/2006 | Jackson et al. |
| 2006/0228391 A1 | 10/2006 | Seyedin et al. |
| 2006/0241339 A1 | 10/2006 | Cook et al. |
| 2006/0266369 A1 | 11/2006 | Atkinson et al. |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102004 A1 | 5/2007 | Nelson et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0144539 A1 | 6/2007 | Dineen et al. |
| 2007/0190108 A1 | 8/2007 | Datta et al. |
| 2007/0204866 A1 | 9/2007 | Conrad et al. |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0267027 A1 | 11/2007 | Nelson et al. |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson et al. |
| 2008/0053461 A1 | 3/2008 | Dineen et al. |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Henri Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |

(56) References Cited

U.S. PATENT DOCUMENTS

| | | |
|---|---|---|
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau et al. |
| 2010/0030011 A1 | 2/2010 | Weadock et al. |
| 2010/0037901 A1 | 2/2010 | Rousseau et al. |
| 2010/0049227 A1* | 2/2010 | Hegde et al. ............ 606/167 |
| 2010/0080791 A1 | 4/2010 | Rousseau et al. |
| 2010/0106246 A1 | 4/2010 | Rousseau et al. |
| 2010/0108077 A1 | 5/2010 | Lindh et al. |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0158854 A1 | 6/2010 | Puisais |
| 2010/0163056 A1 | 7/2010 | Tschopp et al. |
| 2010/0211184 A1 | 8/2010 | Rousseau et al. |
| 2010/0234794 A1 | 9/2010 | Weadock et al. |
| 2010/0234946 A1 | 9/2010 | Rousseau |
| 2010/0256443 A1 | 10/2010 | Griguol |
| 2010/0294284 A1 | 11/2010 | Hohenhorst et al. |
| 2010/0319710 A1 | 12/2010 | Sharkawy et al. |
| 2011/0054522 A1 | 3/2011 | Lindh et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |
| 2011/0238111 A1 | 9/2011 | Frank |
| 2011/0245850 A1 | 10/2011 | Cheng et al. |
| 2011/0282386 A1 | 11/2011 | Friedrich |
| 2012/0123449 A1 | 5/2012 | Schaller et al. |
| 2012/0160249 A1 | 6/2012 | Garrett |
| 2012/0245629 A1 | 9/2012 | Gross et al. |
| 2013/0074849 A1 | 3/2013 | Rousseau et al. |
| 2013/0098371 A1 | 4/2013 | Rousseau et al. |
| 2013/0103078 A1 | 4/2013 | Crovella et al. |
| 2013/0118505 A1 | 5/2013 | Rousseau et al. |
| 2013/0133669 A1 | 5/2013 | Rousseau |
| 2013/0150872 A1 | 6/2013 | Rousseau |
| 2013/0174857 A1 | 7/2013 | Rousseau et al. |
| 2013/0186412 A1 | 7/2013 | Weadock et al. |
| 2013/0319427 A1 | 12/2013 | Sung et al. |

FOREIGN PATENT DOCUMENTS

| | | |
|---|---|---|
| CN | 102198010 | 9/2011 |
| CN | 102198010 A | 9/2011 |
| CN | 102271624 A | 12/2011 |
| DE | 10245076 | 4/2004 |
| DE | 10245076 A1 | 4/2004 |
| EP | 2145587 | 1/2010 |
| EP | 2145587 A2 | 1/2010 |
| EP | 2386252 A1 | 11/2011 |
| EP | 2517633 | 10/2012 |
| EP | 2517633 A1 | 10/2012 |
| FR | 2651113 | 3/1991 |
| FR | 2651113 A1 | 3/1991 |
| JP | 2007-512090 | 5/1982 |
| JP | 11-514266 | 12/1999 |
| JP | 11-514266 | 5/2001 |
| JP | 2001-145646 | 5/2001 |
| JP | 2003265621 | 9/2003 |
| JP | 2006-508708 | 3/2006 |
| JP | 2001-145646 | 7/2006 |
| JP | 2006-517115 | 7/2006 |
| JP | 2006-517115 | 5/2007 |
| JP | 2007-512090 | 5/2007 |
| JP | 2007-313337 | 12/2007 |
| JP | 2008-526286 | 7/2008 |
| JP | 2008-529608 | 8/2008 |
| JP | 2009-006090 A | 1/2009 |
| JP | 2011-530385 | 12/2011 |
| RU | 2005447 C1 | 1/1994 |
| RU | 2202313 C2 | 4/2003 |
| SU | 927236 B | 5/1982 |
| SU | 1697792 A1 | 12/1991 |
| SU | 927236 | 4/1997 |
| WO | WO 97/13465 | 4/1997 |
| WO | WO 99/00058 A1 | 1/1999 |
| WO | WO 00/66050 | 11/2000 |
| WO | WO 01/21107 A1 | 3/2001 |
| WO | WO 03/096928 A1 | 11/2003 |
| WO | WO 03096928 | 11/2003 |
| WO | WO 2004/016196 | 2/2004 |
| WO | WO 2004/016196 A2 | 2/2004 |
| WO | WO 2004/016196 A3 | 2/2004 |
| WO | WO 2004/016196 | 3/2004 |
| WO | WO 2004/020492 | 3/2004 |
| WO | WO 2004/021869 A2 | 3/2004 |
| WO | WO 2004/021870 A2 | 3/2004 |
| WO | WO 2004/021870 A3 | 3/2004 |
| WO | WO 2004/060311 A2 | 7/2004 |
| WO | WO 2004/060311 A3 | 7/2004 |
| WO | WO 2004/084709 A2 | 10/2004 |
| WO | WO 2004/084709 A3 | 10/2004 |
| WO | WO 2004/103196 | 12/2004 |
| WO | WO 2005/046554 A2 | 5/2005 |
| WO | WO 2005/046554 A3 | 5/2005 |
| WO | WO 2005/051292 A2 | 6/2005 |
| WO | WO 2005/082452 A1 | 9/2005 |
| WO | WO 2005/122954 A1 | 12/2005 |
| WO | WO 2006/012188 A1 | 2/2006 |
| WO | WO 2006/072571 A1 | 7/2006 |
| WO | WO 2006/108145 A1 | 10/2006 |
| WO | WO 2007/056583 A1 | 5/2007 |
| WO | WO 2007/075394 A2 | 7/2007 |
| WO | WO 2007/075394 A3 | 7/2007 |
| WO | WO 2007/132449 A2 | 11/2007 |
| WO | WO 2007/132449 A3 | 11/2007 |
| WO | WO 2007/134005 A1 | 11/2007 |
| WO | WO 2007/146338 A2 | 12/2007 |
| WO | WO 2007/149469 A2 | 12/2007 |
| WO | WO 2007/149469 A3 | 12/2007 |
| WO | WO 2008/042058 | 4/2008 |
| WO | WO 2008/063218 | 5/2008 |
| WO | WO 2008/118913 | 10/2008 |
| WO | WO 2009/023256 A2 | 10/2008 |
| WO | WO 2009/036094 A2 | 2/2009 |
| WO | WO 2009036094 A2 | 3/2009 |
| WO | WO 2009036094 A3 | 3/2009 |
| WO | WO 2010/019376 | 2/2010 |
| WO | WO 2010/019376 A2 | 2/2010 |
| WO | WO 2010/035303 | 4/2010 |
| WO | WO 2010/035303 A1 | 4/2010 |
| WO | WO 2010/051195 | 5/2010 |
| WO | WO 2012/004758 | 1/2012 |
| WO | WO 2012/041205 | 4/2012 |
| WO | WO 2012/041205 A1 | 4/2012 |
| WO | WO 2012/064902 | 5/2012 |
| WO | WO 2012/064902 A2 | 5/2012 |
| WO | WO 2012/170468 | 12/2012 |
| WO | WO 2012/170468 A1 | 12/2012 |

OTHER PUBLICATIONS

Harries et al., "The Surgical treatment of snoring", J. of Laryngology and Otology, vol. 110, Issue 12 pp. 1105-1106 (1996).

Huang et al., "Biomechanics of snoring", Endeavour, vol. 19(3): pp. 96-100 (1995).

Pang, Kenny et al., "Tongue Suspension Suture in Obstructive Sleep Apnea", Operative Techniques in Otolaryngology, vol. 17, No. 4, pp. 252-256 (2006).

Repose Genioglossus Advancement, INFLUENT Medical, www.influ-ent.com, 1 page (2008).

Schleef et al., "Cytokine Activation of Vascular Endothelium, Effects on Tissue-Type 1 Plasminogen Activator Inhibitor" The J. of Biological Chem., vol. 263, No. 12, pp. 5797-5803 (1988).

(56) References Cited

OTHER PUBLICATIONS

Schwab et al., "Upper airway and soft tissue changes induced by CPAP in normal subject", Am. J. Respit. Crit. Care Med., vol. 154, No. 4 pp. 1106-1116 (1996).
Schwartz et al., "Effects of electrical stimulation to the soft palate on snoring and obstructive sleep apnea", J. Prosthetic Dentistry, vol. 76 pp. 273-281 (1996).
Shamsuzzaman et al., "Obstructive Sleep Apnea; Implications for Cardiac and Vascular Disease", JAMA vol. 290, No. 14 pp. 1906-1914 (2003).
Teles et al., "Use of Palatal Lift Prosthesis on Patient Submitted to Maxillectomy: A Case Report", Applied Cancer Res. vol. 25(3), pp. 151-154 (2005).
The Advance System, Aspire Medical, Inc. www.aspiremedical.com, 3 pp (2008).
The Pillar Procedure, Restore Medical, Inc. www.restoremedical.com, 2 pp (2008).
Vicente et al., "Tongue-Base Suspension in Conjunction with Uvulopapatopharyngoplasty for Treatment of Severe Obstructive Sleep Apnea: Long-term Follow-Up Results", The Laryngoscope, vol. 116 pp. 1223-1227 (2006).
Wassmuth et al., "Cautery-assisted palatal stiffening operation for the treatment of obstructive sleep apnea syndrome", Otolaryngology—Head and Neck Surgery, vol. 123, pp. 55-60 (2000).
Wiltfang et al., "First results on daytime submandibular electrostimulation of suprahyoidal muscles to prevent night-time hypopharyngeal collapse in obstructive sleep apnea syndrome", Intl J. of Oral & Maxillofacial Surgery vol. 28 pp. 21-25 (1999).
U.S. Appl. No. 13/486,293, filed Jun. 1, 2012.
Database WPI Week 198312, Thomson Scientific, London, GB; AN 1983-D9513K XP002693421, -& SU 927 236 A1 (Petrozazodsk Univ) May 15, 1982 abstract (see figures 7 & 8).
Friedman et al., "A System and Method for Inserting a Medical Device for Treatment of Sleep Apnea via the Nasal Passage, and Device Therefor", Dec. 29, 2008, U.S. Appl. No. 61/203,758, p. 8 & p. 6/8.
MacMillan Dictionary, Fiber, MacMillan Publisher, Liminted 2009-2014.
Medtronic AIRvance System for Obstructive Sleep Apnea. http://www.medtronic.com/for-healthcare-professionals/products-therapies/ear-nose-throat/sleep-disordered-breathing-products/airvance-system-for-obstructive-sleep-apnea/index.htm.
International Search Report re: PCT/US2012/0565677 dated Nov. 27, 2012.
International Search Report dated Apr. 9, 2013 for International Patent Application No. PCT/US2012/061569.
International Search Report dated Apr. 2, 2013 for International Patent Application No. PCT/US2012/067708.
International Search Report dated Oct. 2, 2013 re: PCT/US2013/043238.
International Search Report dated May 24, 2013 for International Patent Application No. PCT/US2012/066011.
Written Opinion dated Nov. 27, 2012 for International Patent Application No. PCT/US2012/056577.

\* cited by examiner

METHODS AND DEVICES FOR TREATMENT OF OBSTRUCTIVE SLEEP APNEA

This application is a continuation of and claims priority to U.S. patent application Ser. No. 12/228,681 filed Aug. 14, 2008. The complete disclosures of the aforementioned related U.S. patent applications are hereby incorporated herein by reference for all purposes.

FIELD OF THE INVENTION

The present invention relates generally to the surgical treatment of obstructive sleep apnea, and more particularly, to the use of implants to prevent pharyngeal wall collapse or to provide altered airway geometries to prevent possible airway obstruction during sleep.

BACKGROUND OF THE INVENTION

Several forms of sleep apnea have been identified. Obstructive sleep apnea (OSA) is caused by a blockage of the airway, usually when the soft tissue in the throat collapses and closes during sleep. Less common forms of sleep apnea include central sleep apnea (CSA), wherein the airway is not blocked but the brain fails to signal the muscles to breathe, and mixed apnea which, as the name implies, is a combination of OSA and CSA.

As shown in FIG. 1a, an air passage 140a of a patient 101a is open while the patient is in the awake state. The soft tissue components, including the soft palate 130a and the pharyngeal walls 132a of the air passage are supported by the underlying musculature to maintain the passageway in the open condition. During an obstructive sleep apnea event, illustrated in FIG. 1b, the air passage 140b of a patient 101b is partially or completely blocked by surrounding soft tissue 130b, 132b, which has collapsed due to the relaxation of the supporting musculature and has been displaced during sleep by gravity or other forces.

With each apnea event, the brain briefly arouses the sleeping person in order to resume breathing, but sleep is consequently extremely fragmented and of poor quality. Untreated, sleep apnea can cause high blood pressure, cardiovascular disease, memory problems, weight gain, impotency, and headaches. Moreover, untreated sleep apnea may be responsible for job impairment, motor vehicle crashes, and marital discord.

According to the National Institutes of Health, sleep apnea is very common, as common as adult diabetes, and affects more than twelve million Americans. The factors that increase the risk of having OSA include being male, overweight, and over the age of forty, but sleep apnea can strike anyone at any age, even children. Because of the lack of awareness by the public and healthcare professionals, the vast majority of patients remain undiagnosed and therefore untreated, despite the fact that this serious disorder can have significant consequences.

Attempts to provide an effective treatment for obstructive sleep apnea have yielded unsatisfactory results. For example, electrical stimulation of the soft palate has been suggested to treat snoring and obstructive sleep apnea. Such a teaching is found in Schwartz et al., "Effects of electrical stimulation to the soft palate on snoring and obstructive sleep apnea," J. Prosthetic Dentistry, pp. 273-281 (1996). Devices to apply electrical stimulation are described in U.S. Pat. Nos. 5,284,161 and 5,792,067. Electrical stimulation to treat sleep apnea is also discussed in Wiltfang et al., "First results on daytime submandibular electrostimulation of suprahyoidal muscles to prevent night-time hypopharyngeal collapse in obstructive sleep apnea syndrome," International Journal of Oral & Maxillofacial Surgery, pp. 21-25 (1999). Such devices are appliances requiring patient adherence to a regimen of use as well as subjecting the patient to discomfort during sleep and repeated arousals during deep sleep.

Continuous Positive Airway Pressure (CPAP) has recently been adopted as a useful, albeit cumbersome, means of preventing sleep apnea. CPAP delivers air into the airway through a specially designed nasal mask or pillows. The mask does not breathe for the patient; the flow of air creates enough pressure when the patient inhales to keep the airway open. In effect, a pneumatic splint is formed in the airway. CPAP is considered the most effective non-surgical treatment for the alleviation of snoring and obstructive sleep apnea. Compliance, however, is only 50%, as patients complain about discomfort from the mask, hoses, etc. and that the equipment requires maintenance. Additionally, patients complain of discomfort such as bloating, nasal drying, and dry eyes.

Surgical treatments have also been employed. One such treatment is uvulopalatopharyngoplasty (UPPP). UPPP is discussed, for example, in Harries et al., "The surgical treatment of snoring," Journal of Laryngology and Otology, pp. 1105-1106 (1996), which describes removal of up to 1.5 cm of the soft palate. The use of UPPP in the treatment of snoring is assessed in Cole et al., "Snoring: A review and a Reassessment," Journal of Otolaryngology, pp. 303-306 (1995). In that procedure, about 2 cm of the trailing edge of the soft palate is removed through the use of a scalpel, laser or other surgical instrument, thereby reducing the tendency of the soft palate to flutter between the tongue and the pharyngeal wall of the throat. The procedure is frequently effective to alleviate snoring but has demonstrated limited effectiveness in moderate or severe apnea. The procedure is painful and frequently results in undesirable side effects. In particular, the reduction of the soft palate compromises the ability of the soft palate to seal off nasal passages during swallowing and speech. In an estimated 25% of uvulopalatopharyngoplasty patients, fluid escapes from the mouth into the nose while drinking.

Uvulopalatopharyngoplasty (UPPP) may involve lasting discomfort. For example, scar tissue on the soft palate may present a continuing irritant to the patient. In addition, UPPP is not reversible and may induce adverse side effects not justified by the benefits of the surgery. Furthermore, UPPP is targeted to the correction of deficiencies associated with the palate only and does not address issues associated with the collapse of the tongue and lateral pharyngeal walls.

Radiofrequency ablation of the soft palate, or Somnoplasty$^{SM}$, is similar in concept to the Laser Assisted Uvulopalatopharyngoplasty (LAUP), although a different energy source is used, and thermal lesions are produced within the tissues, rather than using a laser to ablate the tissue surface. For that reason, radiofrequency ablation appears to be growing in popularity as an alternative to LAUP. The Somnoplasty$^{SM}$ device is approved by the U.S. Food and Drug Administration (FDA) for radiofrequency ablation of palatal tissues for simple snoring and radiofrequency ablation of the base of the tongue for OSA. In some situations, radiofrequency ablation of the soft palate and base of tongue are performed together as a multi-level procedure. To date, the treatments alone or in combination have failed to provide relief to more than 50% of patients.

Another device intended to treat snoring or obstructive sleep apnea is comprised of several braided PET cylinders that are implanted to make the tissues of the tongue or uvula more rigid and less prone to deflection against the pharyngeal wall. The Pillar™ Palatal Implant System, marketed by Restore Medical of St Paul, Minn., is an implantable device that has been cleared by the FDA 510(k) process. The device is a cylindrical-shaped segment of braided polyester filaments that is permanently implanted submucosally in the soft palate. The labeled indication of the device is as follows: "The Pillar™ Palatal Implant System is intended for the reduction of the incidence of airway obstructions in patients suffering from mild to moderate OSA (obstructive sleep apnea)." The device has been associated with a number of adverse side effects, including extrusion, infection, and patient discomfort.

The Repose™ device, marketed by Influent Medical LLC of Concord, N.H., involves the use of a titanium screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to collapse against the posterior pharyngeal wall during sleep. The reported duration of beneficial effects afforded by the implant is less than a year. Due to the high activity of the tongue during wakefulness, the suture component of this device has been shown in some cases to act as a "cheese cutter" to the tongue, causing device failure and requiring subsequent removal.

Magnets have also been considered as implants for the treatment of obstructive sleep apnea. These devices are currently being evaluated in clinical trials. One serious complication than can potentially occur with these implants is implant migration or flipping of the magnets which can cause acute airway closure.

In summary, electrical stimulation of the musculature within the airway is ineffective since it arouses the patient from deep sleep. CPAP effectively manages OSA but has a very low patient compliance (less than 50% of patients continue the treatment). Surgical techniques and implants have also been evaluated, yet still do not provide a satisfactory and lasting solution. No one device seems capable of treating the multi-causal problem of obstructive sleep apnea. What is needed are methods and devices that reduce the burden of managing obstructive sleep apnea through a minimally invasive approach that provides long term and effective results. Ideally, the treatment should be adjustable and removable if necessary. The inventions described herein provide such treatments that offer long-term relief of OSA.

SUMMARY OF THE INVENTION

The present invention is directed to systems and methods for treating obstructive sleep apnea. One embodiment of the invention is a method for surgically treating obstructive sleep apnea, comprising the step of implanting a device into tissue space located beneath a pharyngeal wall to alter a shape of the pharyngeal wall. In one embodiment, the device retracts or alters the shape of the pharyngeal wall to resist collapse. In another embodiment, the device alters the geometry of the airway to prevent complete obstruction of the pharyngeal tissues during sleep.

The device is a retractor that has a self-supporting tissue engaging element that controls the position of the soft tissues beneath the pharyngeal wall during sleep and allows for tissue ingrowth. The tissue engaging element may, for example, be a biocompatible mesh or other suitable porous fabric. The tissue engaging element may be made through typical processing means including, but not limited to, fiber knitting, weaving, braiding, non-woven production, expansion methods (such as ePTFE) or perforation of film type products, melt blowing, extrusion, carding, or injection molding. The retractor is generally of a "sheet like" or planar shape, with the width, length and thickness dimensions of the retractor typically not equal.

The retractor may be introduced orally and implanted through the pharyngeal wall into the tissue beneath the pharyngeal wall. The retractor may alternatively be introduced through a side of a patient's neck. The retractor is placed within the soft tissues of the neck, either within tissue planes or crossing them, as deemed appropriate by the surgeon to produce sufficient refraction or alteration of the lumen of the affected region of the airway.

One embodiment of the invention is a device for altering a shape of a pharyngeal wall by implantation of the device in tissue beneath the pharyngeal wall. The device comprises a retracting element having a constrained configuration and an unconstrained configuration different from the constrained configuration, and a tissue engaging element connected to the retracting element, the tissue engaging element adapted for engaging the tissue beneath the pharyngeal wall. A shape of the pharyngeal wall is altered when the retracting element reverts from the constrained configuration to the unconstrained configuration.

Another embodiment of the invention is a method for surgically treating obstructive sleep apnea. The method includes the steps of delivering an implantable device into tissue located beneath a pharyngeal wall, and engaging the tissue beneath the pharyngeal wall with the implantable device to alter a shape of the pharyngeal wall.

The invention is further embodied by a system for treating obstructive sleep apnea by altering a shape of a pharyngeal wall. The system comprises an implantable device including a tissue engaging element and a retracting element, and a hand-held delivery system comprising a hand-piece, an actuating lever moveably connected to the hand-piece, a shaft extending distally from the hand-piece, a housing disposed at a distal end of the shaft for storing at least one implantable device, and a deployment device activatable by the lever for deploying the implantable device through the pharyngeal wall into tissue space located beneath the pharyngeal wall so as to alter a shape of the pharyngeal wall.

Another embodiment of the invention is a device for retracting a pharyngeal wall. The device includes an elongate fibrous member having a central portion for engagement with the pharyngeal wall, and having first and second retracting portions extending from the central portion, each of the first and second retracting portions having features for engaging tissue in the neck and exerting a tensile retraction force on the central portion.

DETAILED DESCRIPTION OF THE INVENTION

The present invention is directed to a device and method of implantation that can be used to treat obstructive sleep apnea. The device can be implanted into tissue beneath the pharyngeal wall using several implantation methods described herein. The term "beneath the pharyngeal wall" refers to a space beneath the pharyngeal wall that does not exist naturally but is formed during the implantation step. The newly formed space allows the device to be implanted next to the back of the pharyngeal wall (the side that does not face the airway) and against the prevertebral fascia and musculature such as the longus capitus muscles. The device, referred to herein as a retractor or simply as the "device," may include a flexible backing or arch-shaped retracting element attached to a tissue engaging element. The device is used to alter a characteristic of the pharyngeal wall. For example, the device may provide additional retraction means on the lateral pharyngeal walls or maintain an altered shape of the airway. The device of the invention provides retraction or support of the pharyngeal walls to allow air to flow past any obstruction that may be apparent if the pharyngeal walls are collapsed. It may also be used to change the shape of the pharyngeal airway.

Figure 1A:
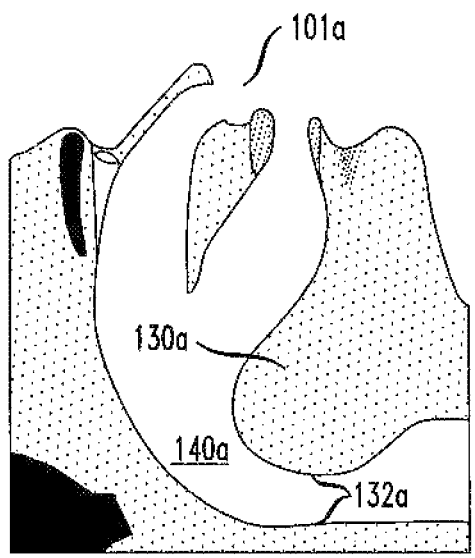
FIGS. 1a and 1b are schematic cross-sectional representations of a patient's upper airway.
Figure 1B:
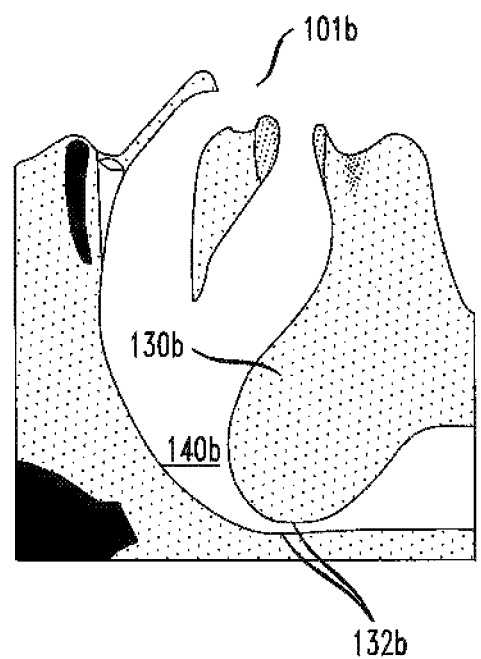
Figure 2:
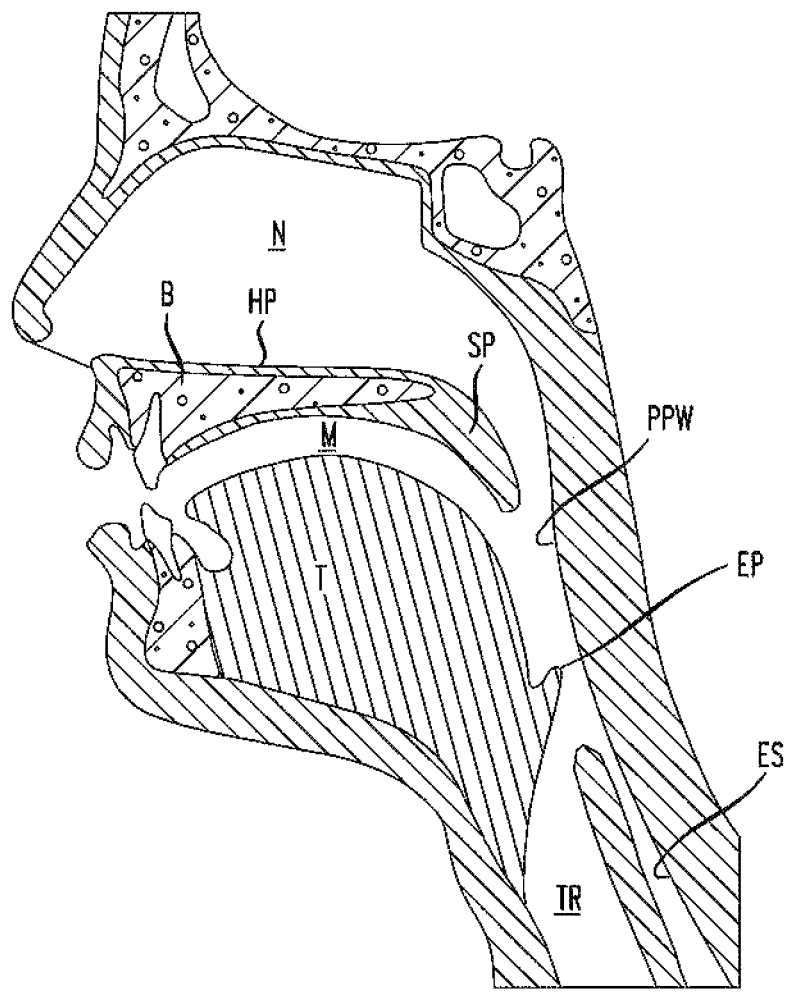
FIG. 2 is a schematic cross-sectional representation of a patient's upper airway.

FIG. 2 illustrates a cross-section of a patient's head with anatomical structures such as the nasal sinuses (N), bone (B) of the hard palate (HP), soft palate (SP), mouth (M), tongue (T), trachea (TR) epiglottis (EP), esophagus (ES) and posterior pharyngeal wall (PPW). The lateral pharyngeal walls (not shown in this illustration) are, as the name implies, lateral to the posterior pharyngeal wall. According to imaging studies on CPAP users described by Schwab et al., "Upper airway and soft tissue changes induced by CPAP in normal subjects," Am. J. Respir. Crit. Care Med., Vol 154, No. 4, October 1996, 1106-1116, the lateral pharyngeal walls are more "compliant" than the soft palate and tongue. Those studies provide evidence that the lateral pharyngeal walls play an important role in mediating upper airway caliber. In certain disclosed embodiments, the intent of the implantable devices described herein is to retract the pharyngeal walls laterally. The lateral retraction serves to prevent collapse of these soft tissue structures and to maintain an airway for the patient, particularly when the diaphragm descends during inhalation and causes excessive negative pressure that might act to collapse the pharyngeal walls. In certain other disclosed embodiments, the intent of the implantable device is to provide altered geometries of the airway during inhalation that are unable to occlude due to mismatched geometries between the mating tissues, more particularly the base of the tongue and the posterior and or lateral pharyngeal walls.

Figure 3A:
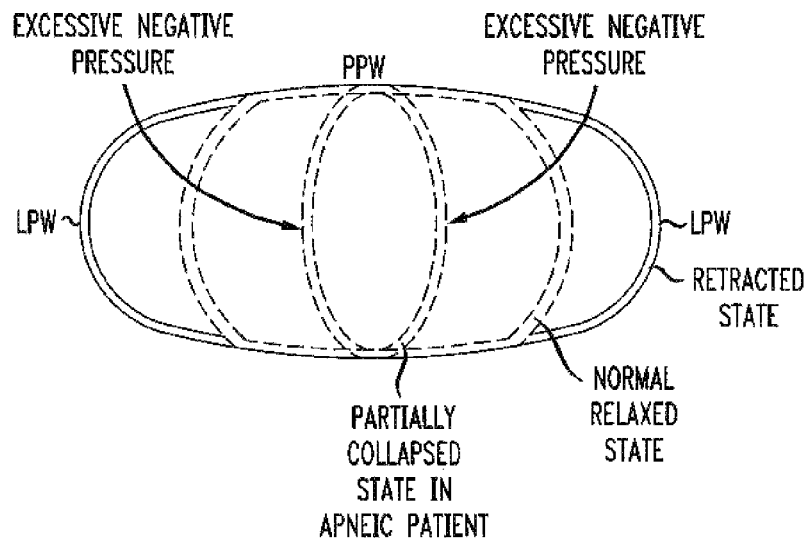
FIG. 3a is a cross-sectional view of a pharyngeal wall showing several superimposed states of the wall.
Figure 3B:
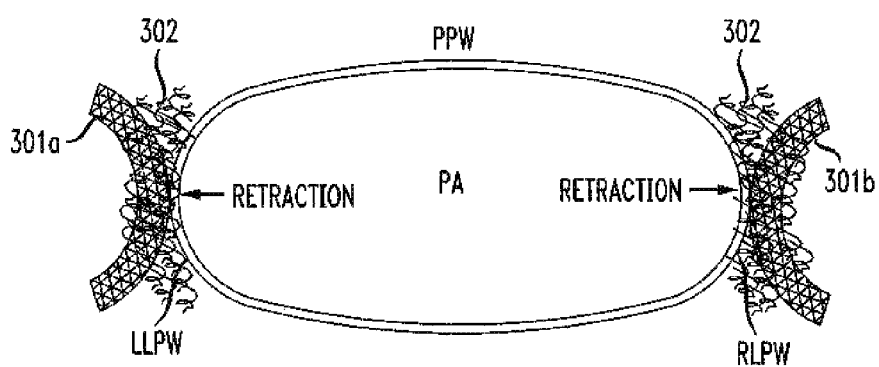
FIG. 3b is a cross-sectional view of a pharyngeal wall showing two pharyngeal retractors implanted according to one embodiment of the invention.

FIG. 3a illustrates a cross-section of the pharynx at the oropharyngeal level, including the posterior pharyngeal wall (PPW) and lateral pharyngeal walls (LPW). The oropharynx is shown in solid lines in its distended (retracted) state, and is shown in dashed lines in a normal relaxed state and in a partially collapsed state. As shown in FIG. 3b, a pair of implantable devices 301a, 301b in accordance with the invention causes the left (LLPW) and right (RLPW) lateral walls of the pharynx to resist the negative pressure produced by the descending diaphragm, thereby keeping the airway open. Subsequent tissue engagement with the implantable device and tissue ingrowth 302 into the device serve to secure the mesh strip, and therefore, to stabilize the retracted state.

Figure 4:
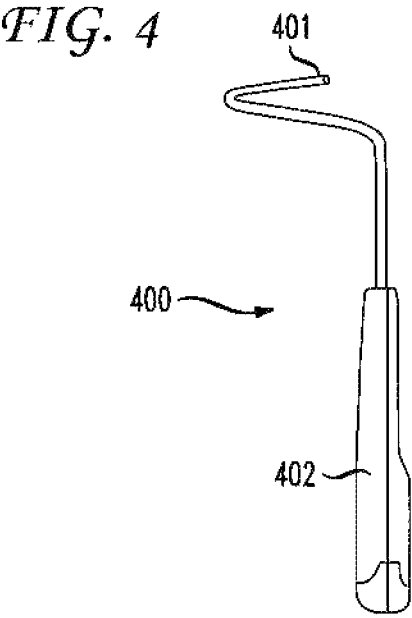
FIG. 4 is a plan view of a trocar according to one embodiment of the invention.

One embodiment of the invention is an implantable device that is releasably attached to at least one trocar. FIG. 4 illustrates a trocar 400 having a distal end 401 and a handle 402 on the proximal end. The distal end 401, with the implantable device attached, is passed through the pharyngeal wall and into the tissue underneath the pharyngeal wall. The implantable device is then placed in the formed space beneath the pharyngeal wall.

The trocar 400 may optionally have a Doppler probe (not shown) that allows detection of blood flow in any arterial structures located near the target tissues. The probe may be embedded within the distal tip 401 so as to help navigate the tissue and avoid damaging blood vessels, particularly when an approach is utilized whereby the implantable device is installed across multiple tissue planes within the affected regions of the neck.

In addition to the minimally invasive approach using a trocar, the device may alternatively be placed beneath the pharyngeal wall using an open, direct approach to the pharyngeal wall from the side of a patient's neck. A single device or more than one of the devices can be used to treat the patient.

Figure 5:
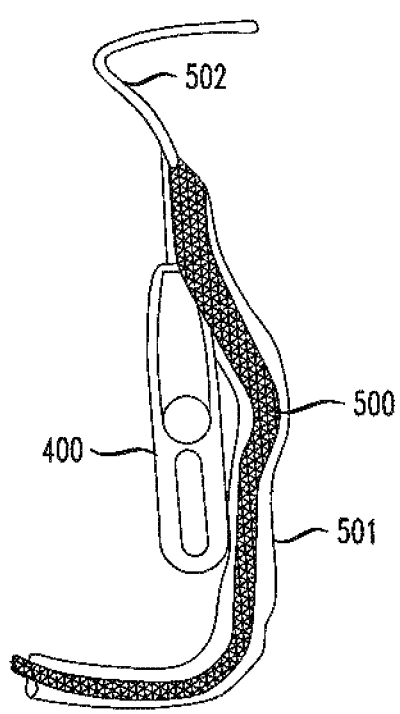
FIG. 5 is a plan view of a pharyngeal retractor implant system according to another embodiment of the invention.

FIG. 5 illustrates an exemplary attachment of a mesh device 500 to the trocar 400. The mesh device 500 is fixed to a proximal end of a plastic trocar sleeve 502 that covers the distal end of the trocar. The fixation of the mesh to the end of the plastic trocar sleeve can be achieved through the use of wrapping, welding, gluing, tying, clips or other suitable means. In one embodiment, the device 500 is a mesh made from polypropylene or another porous biocompatible material selected for its tissue engaging properties.

In the embodiment shown, the implantable device 500 is covered by a protective sheath 501. Polymers such as expanded polytetrafluoroethylene (ePTFE), polyethylene terephalate (PET), PVDF, polyesters, polyolefins, silicones or polyurethanes are utilized in the construction of the protective sheath. The materials and construction techniques of the protective sheath are chosen so as to minimize friction and engagement of the sheath with surrounding tissue. The purpose of the protective sheath 501 is to minimize tissue drag on the implantable device during insertion and to prevent any abrasion or irritation of non-target tissues during placement of the device.

In use, the distal end 401 (FIG. 4) of the trocar penetrates the pharyngeal wall at or near a lateral or posterior portion of the wall. If necessary, the insertion of the trocar may be facilitated through the use of an incision made just prior to the implantation step. The site of incision and orientation of the device will be determined by the surgeon and will be dependent on the individual patient anatomy and the site of pharyngeal collapse. Alternatively, the trocar 400 may have a sharpened edge at its distal end 401 for piercing the mucosal surface of the pharyngeal wall. The trocar is then used to pass the mesh device 500 through the pharyngeal wall and to deposit the device in the tissue beneath the pharyngeal wall. In one embodiment, after penetrating the pharyngeal wall and passing through the tissue beneath the pharyngeal wall, the trocar tip is passed through the pharyngeal wall again at a second location, passing from underneath the wall to within the airway. The mesh is then drawn through the tissue using the plastic trocar sleeve, with the protective sheath surrounding the mesh to protect the tissue. The plastic trocar sleeve and the protective sheath are then removed. If the pharyngeal retractor is longer than necessary, it is trimmed to length while under slight tension to reduce the length that remains within the pharyngeal wall. The incisions in the pharyngeal wall are then closed with suture, clips, or biocompatible tissue adhesive.

Figure 6A:
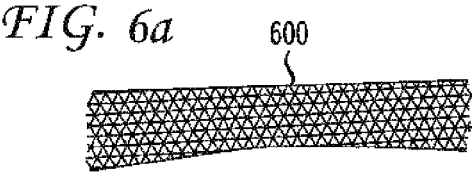
FIGS. 6a-6f are views of several pharyngeal retractors according to various embodiments of the invention.

FIG. 6a illustrates one embodiment of an implantable device according to the invention. The device comprises a tissue engaging element shown in FIG. 6a as a length of mesh 600. In the embodiment of FIG. 6a, no other material is attached or associated with the mesh. The tissue engaging element is implantable into the space beneath the pharyngeal wall. The element is constructed to frictionally or otherwise engage surrounding tissue upon implantation, and to thereby resist movement after placement within the tissue.

The biocompatible tissue engaging element 600 is further receptive to tissue ingrowth in the form of scar tissue that embeds during healing and becomes integrated with the mesh. That scar tissue reinforces the overall tissue mass in which the tissue engaging element is implanted. The element may encourage structural ingrowth of surrounding tissue, and may also encourage cellular ingrowth of tissue.

Many medical textile designs are known to those skilled in the art of making mesh, fabrics, non-wovens, etc. for hernia repair. Medical textile products are based on fabrics, of which there are four types: woven, knitted, braided, and nonwoven. The first three of these are made from yarns, whereas the fourth can be made directly from fibers, or even from polymers such as Gore-Tex®-based products or electrostatically spun materials from polyurethane. There is, therefore, a hierarchy of structure: the performance of the final textile product is affected by the properties of polymers whose structures are modified at between two and four different levels of organization.

Of the many different types of polymers, only a few can be made into useful fibers. This is because a polymer must meet certain requirements before it can be successfully and efficiently converted into a fibrous product. For example, the polymer chains should be linear, long, and flexible. Side groups of the polymers should be simple, small, or polar. Polymers should be dissolvable or meltable for extrusion. Chains should be capable of being oriented and crystallized.

Common fiber-forming polymers include cellulosics (linen, cotton, rayon, acetate), proteins (wool, silk), polyamides, polyester (PET), olefins, vinyls, acrylics, polytetrafluoroethylene (PTFE), polyphenylene sulfide (PPS), aramids (Kevlar, Nomex), and polyurethanes (Lycra, Pellethane, Biomer). Each of these materials is unique in chemical structure and potential properties. For example, among the polyurethanes is an elastomeric material with high elongation and elastic recovery, whose properties nearly match those of elastin tissue fibers. This material—when extruded into fiber, fibrillar, or fabric form—derives its high elongation and elasticity from alternating patterns of crystalline hard units and noncrystalline soft units.

Although several of the materials mentioned above are used in traditional textile as well as medical applications, various polymeric materials—both absorbable and nonabsorbable—have been developed specifically for use in medical products.

The reactivity of tissues in contact with fibrous structures varies among materials and is governed by both chemical and physical characteristics. Absorbable materials typically excite greater tissue reaction, a result of the nature of the absorption process itself. Among the available materials, some are absorbed faster (e.g., polyglycolic acid, polyglactin acid) and others more slowly (e.g., polyglyconate). Semiabsorbable materials such as cotton and silk generally cause less reaction, although the tissue response may continue for an extended time. Nonabsorbable materials (e.g., nylon, polyester, polypropylene) tend to be inert and to provoke the least reaction. To minimize tissue reaction, the use of catalysts and additives is carefully controlled in medical-grade products.

As discussed, of the many types of polymers, only a few can be made into useful fibers that can then be converted into medical textile products. To make fibers, polymers are extruded by wet, dry, or melt spinning and then processed to obtain the desired texture, shape, and size. Through careful control of morphology, fibers can be manufactured with a range of mechanical properties. Tensile strength can vary from textile values (values needed for use in typical textile products such as apparel) of 2-6 g/d (gram/denier) up to industrial values (values typical of industrial products such as tire cords or belts) of 6-10 g/d. For high-performance applications, such as body armor or structural composites, novel spinning techniques can produce fibers with strengths approaching 30 g/d. Likewise, breaking extension can be varied over a broad range, from 10-40% for textile to 1-15% for industrial and 100-500% for elastomeric fibers.

Fibers or filaments are converted into yarns by twisting or entangling processes that improve strength, abrasion resistance, and handling. Yarn properties depend on those of the fibers or filaments as well as on the angle of twist. Yarns are interlaced into fabrics by various mechanical processes, including weaving, knitting, and braiding. There are three prevalent fabric structures used for medical implants or sutures: woven, in which two sets of yarns are interlaced at right angles; knitted, in which loops of yarn are intermeshed; and braided, in which three or more yarns cross one another in a diagonal pattern. Knitted fabrics can be either weft or warp knit, and braided products can include tubular structures, with or without a core, as well as ribbon.

There are also numerous medical uses for nonwoven fabrics (wipes, sponges, dressings, gowns), made directly from fibers that are needle-felted, hydroentangled, or bonded through a thermal, chemical, or adhesive process. Nonwovens may also be made directly from a polymer. Expanded polytetrafluoroethylene (ePTFE) products such as sutures and arterial grafts and electrostatically spun polyurethane used as tubular structures are examples of medical applications of polymer-to-fabric nonwovens.

The properties of fabrics depend on the characteristics of the constituent yarns or fibers and on the geometry of the formed structure. Whether a fabric is woven, knitted, braided, or nonwoven will affect its behavior. Fabrics that are woven are usually dimensionally very stable but less extensible and porous than the other structures. One disadvantage of wovens is their tendency to unravel at the edges when cut squarely or obliquely for implantation. However, the stitching technique known as a Leno weave—in which two warp threads twist around a weft—can substantially alleviate this fraying or unraveling.

Compared with woven fabrics, weft-knitted structures are highly extensible, but they are also dimensionally unstable unless additional yarns are used to interlock the loops and reduce the extension while increasing elastic recovery. Warp-knitted structures are extremely versatile, and can be engineered with a variety of mechanical properties matching those of woven fabrics. The major advantage of knitted materials is their flexibility and inherent ability to resist unraveling when cut. A potential limitation of knitted fabrics is their high porosity, which—unlike that of woven fabrics—cannot be reduced below a certain value determined by the construction. As a result, applications requiring very low porosity usually incorporate woven materials.

Typically employed in cords and sutures, braided structures can be designed using several different patterns, either with or without a core. Because the yarns criss-cross each other, braided materials are usually porous and may imbibe fluids within the interstitial spaces between yarns or filaments. To reduce their capillarity, braided materials are often treated with a biodegradable (polylactic acid) or nonbiodegradable (Teflon®) coating. Such coatings also serve to reduce chatter or noise during body movement, improve hand or feel, and help position suture knots that must be transported by pressure from a surgeon's finger from outside the body to the wound itself.

The properties of nonwoven fabrics are determined by those of the constituent polymer or fiber and by the bonding process. For instance, expanded PTFE products can be formed to meet varying porosity requirements. Because of the expanded nature of their microstructure, these materials compress easily and then expand—a suture, for example, can expand to fill the needle hole made in a tissue—allowing for tissue ingrowth in applications such as arterial and patch grafts. Polyurethane-based nonwovens produce a product that resembles collagenous material in both structure and mechanical properties, particularly compliance (extension per unit pressure or stress). The porosity of both PTFE- and polyurethane-derived nonwovens can be effectively manipulated through control of the manufacturing processes.

In one embodiment of the invention, the tissue engaging element utilized in the implantable device is fabricated by warp knitting a monofilament polypropylene yarn that is approximately 3 to 6 mils in diameter. In one exemplary embodiment, the yarn is 3.5 mils in diameter. In this embodiment, the knitted mesh preferably has 40-80 courses per inch and 7-11 wales per inch. Other designs of medical textiles may also be used.

In addition to the polymeric fibers described above, non-polymeric fibers may be used in constructing woven, braided, knitted and non-woven fabrics for use in the invention. For example, nitinol or stainless steel fibers may be used alone or in combination with other fibers such as polymeric fibers to construct a tissue engaging element having altered retraction properties.

A perforated film-type product (not shown) may alternatively be used in fabricating the tissue engaging element. In that embodiment, a polymer film is perforated with a plurality of holes to engage tissue and to allow tissue ingrowth. The size and spacing of the holes may be optimized for those functions. Further, the size and spacing of the holes may be varied over the film to promote greater tissue engagement in certain locations on the film.

The tissue engaging element may comprise a film having other types of tissue engaging features, alone or in combination with perforations. For example, the film may comprise corrugations, dimples, knurling or other embossed, molded or machined relief patterns that engage tissue that is pressed against the tissue engaging element. Full or partial perforations may include raised edges that engage surrounding tissue.

Figure 6B:
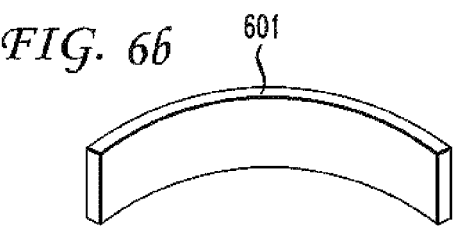

A retracting element shown in FIG. 6b, such as a flexible backing or arch 601, may be used. The retracting element 601 is fabricated from a biocompatible material such as stainless steel, nitinol, silicone, polyethylene, polytetrafluoroethylene, or polypropylene. The retracting element is preferably capable of withstanding a large number of flex cycles without fatigue failure because the element undergoes a strain cycle with each movement of the pharyngeal wall, such as in swallowing and speaking. The retracting element 601 may be produced with a three-dimensional geometry in order to exert specific directional forces when deployed that change one or more characteristics of the pharyngeal wall, as described in more detail below.

In another embodiment, the retracting element may be substantially non-flexible. A non-flexible retracting element may be fabricated from titanium, stainless steel or ceramic. An implantable device including a non-flexible retracting element may be used to maintain a shape of a pharyngeal wall to prevent collapse.

Figure 6C:
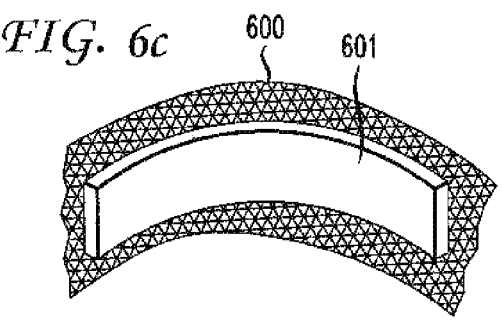

A retracting element 601 may be attached to a tissue engaging element 600, as shown in FIG. 6c, in another embodiment of the invention. The attachment may be by adhesive, suture, clips, staples, screws, or another fastening means such as ultrasonic welding. As noted above, the tissue engaging element engages surrounding tissue after implantation and promotes tissue ingrowth, becoming permanently integrated with the surrounding tissue. As a result, the retracting element 601 becomes permanently fixed in position beneath the pharyngeal wall and will not migrate. The result is that the pharyngeal wall is less likely to collapse during sleep and produce an obstruction to breathing.

In an alternative embodiment of the invention, the tissue engaging element, the retracting element, or both can be at least partially fabricated from resorbable synthetic polymers such as polylactide, polyglactide, polydioxanone, polycaprolactone, or co-polymers thereof. The long-term shape of the soft tissue is provided through the presence of the tissue formed around and through the tissue engaging element as the absorbable component of the implant is resorbed.

Figure 6D:
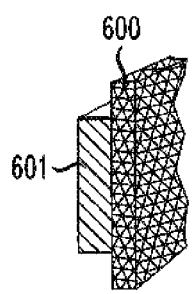
Figure 6E:
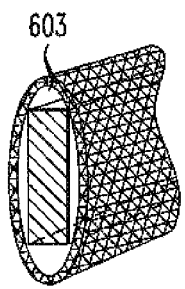
Figure 6F:
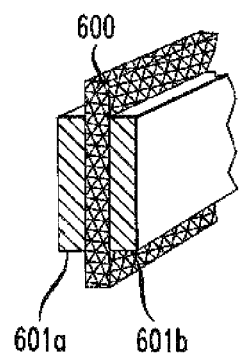

FIGS. 6d-6f are cross-sectional views through several embodiments of a implantable device of the invention incorporating both a mesh tissue engaging element and an arch-shaped retracting element. FIG. 6d is a cross-sectional view of the device of FIG. 6c, wherein one side of the tissue engaging element 601 is attached to a retracting element 601. The tissue engaging element 601 may be attached through the use of adhesives, such as cyanoacrylates, silicones and hot melt polymers. The adhesives may be absorbable or non-absorbable. The tissue engaging element may alternatively be attached through the use of mechanical fixation means such as sutures and clips.

Alternatively, as shown in FIG. 6e, the retracting element may be produced with a reduced width and then passed through or woven into the mesh component. The figure shows an embodiment wherein the flexible arch is encased within a sleeve 603 comprising the tissue engaging element. The retracting element may alternatively comprise holes, slots or other features (not shown) allowing the retracting element to be interwoven into the fabric of the tissue engaging element.

In the embodiment shown in FIG. 6f, the mesh 600 is attached to two retracting elements 601a and 601b, one on each side of the mesh component. All of the embodiments shown may be used to provide sustained retraction or shaping of the pharyngeal wall.

Optionally, image-enhancing substances such as radio-opaque or ultrasonically sensitive materials can be layered onto any of the surfaces of the pharyngeal retractor to aid in imaging of the device during and after deployment. In another embodiment, anti-microbial agents such as triclosan or antibiotics, or pain management medicaments are applied or coated to one or more surfaces of the components that comprise the pharyngeal refractor prior to deployment. Alternatively, the agents may be included in the polymers during the fabrication processes through extrusion, blending, casting, solvent mixing or other typical polymer processing means. The agents may be included within an absorbable component to provide controlled or profiled release of the substances during wound healing.

Figure 7:
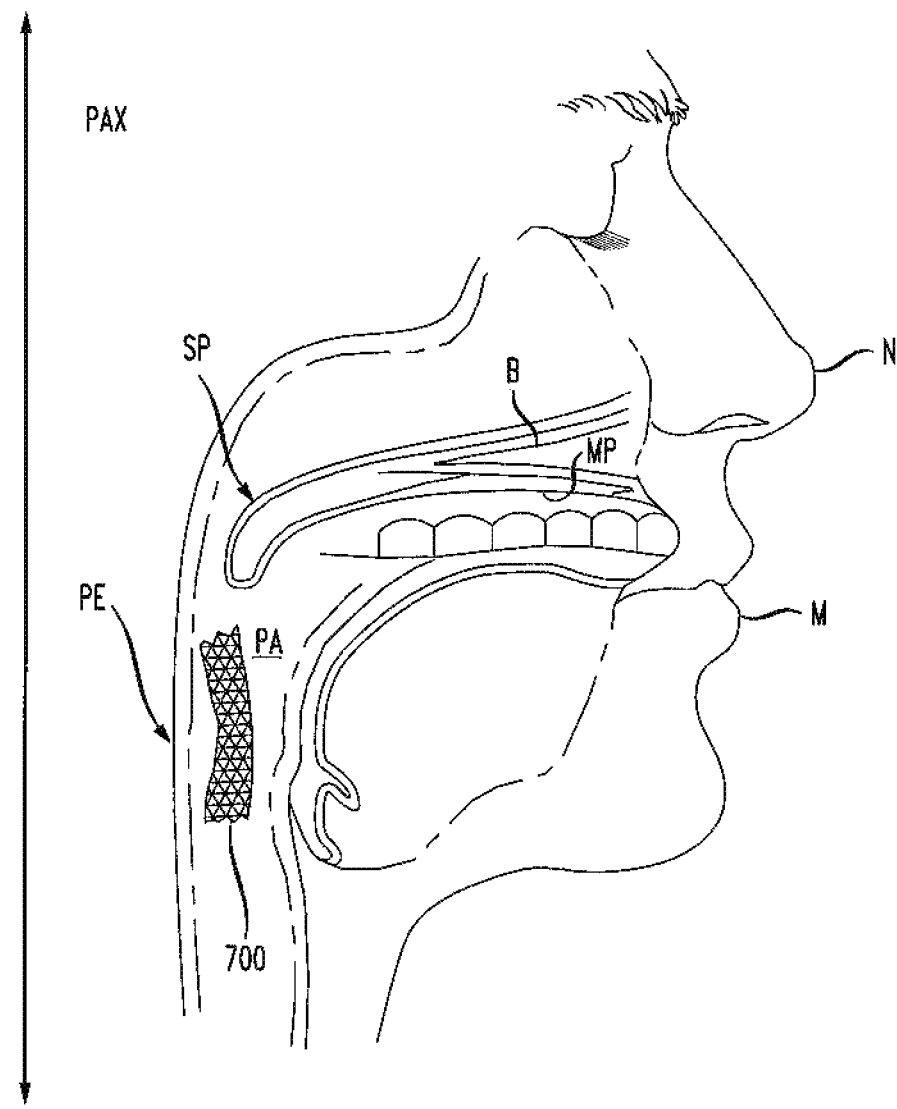
FIG. 7 is a schematic representation of a patient's upper airway showing a pharyngeal retractor implanted according to one embodiment of the invention.
Figure 8:
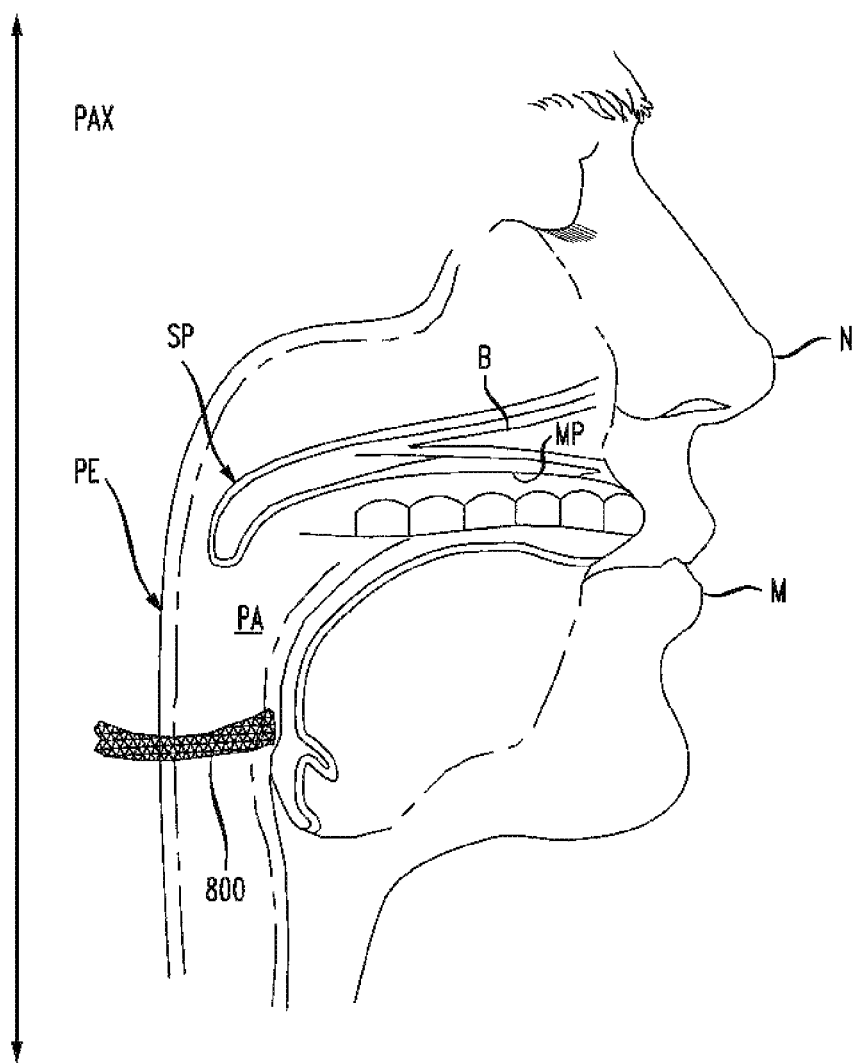
FIG. 8 is a schematic representation of a patient's upper airway showing a pharyngeal retractor implanted according to one embodiment of the invention.

Orientation of the implantable device in the patient may be selected depending on the particular patient anatomy. For example, an elongated device may be placed so that the device ends are in the same plane as the pharynx or in a plane parallel to the pharyngeal axis (PAX), as illustrated by the device 700 shown in FIG. 7; i.e., so that a longitudinal axis of the device is parallel to the pharyngeal axis. Alternatively, the mesh strip may be placed perpendicular to the pharyngeal axis (PAX), as illustrated by the device 800 shown in FIG. 8. In that case, the longitudinal axis of the mesh strip is perpendicular to the pharyngeal axis. In either case, the implantable device (with or without a retracting element) is placed by a surgeon in such a way so as to change the shape of the pharyngeal walls to prevent collapse during inhalation.

In addition to placing the implantable device using a trocar in a minimally invasive approach, the device of the invention may also be placed underneath the pharyngeal wall using an open, direct visualization approach to the pharynx from the side of a patient's neck. A similar approach to the tissue space underneath the pharyngeal wall is used to perform cervical spinal disc replacement. That approach may be used in the present invention on an outpatient basis or one night hospital stay, for example.

The implantable device of the invention may be a retractor 900 (FIG. 9) that is produced as or includes a fibrous element 905 with tissue engaging features 910. The tissue engaging features may be directional frictional features such as the barbs shown in the figure, or may be non-directional frictional features such as those of a textile. Fibrous elements 905 may be produced as a barbed monofilament, as a braided textile structure with frictional elements encased with the braid, as a combination barbed/braided structure, or as a textile or filament having a roughened or high-friction surface.

Figure 9:
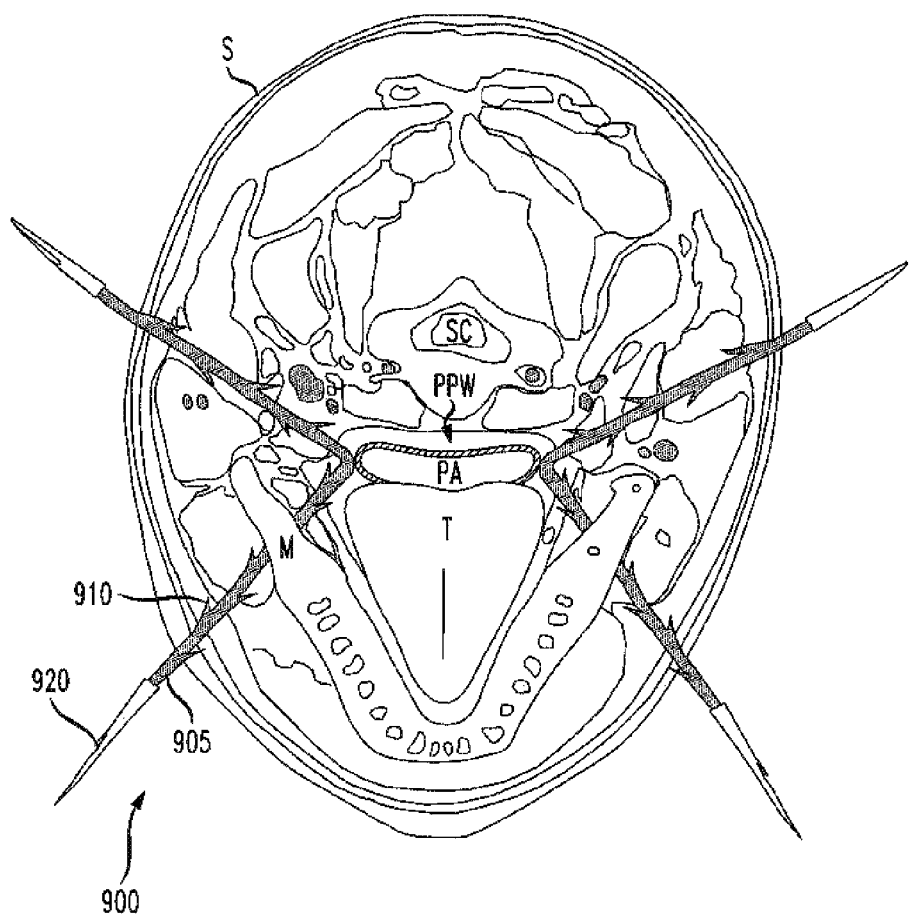
FIG. 9 is a schematic transverse cross-section of a patient's head at a level below the temporal styloid process, showing one embodiment of the invention.

The view of FIG. 9 is a section through a patient's neck showing the tongue T, lower mandible M, skin S, posterior pharyngeal wall PPW and pharyngeal airway PA. The fibrous elements 905 are passed through the pharyngeal wall from within the oral cavity with the two ends of the elements 905 entering a single hole located medially on the lateral aspect of the pharyngeal wall. In the placement, the retractor 900 may be passed in an anterior/posterior orientation and exits the skin of the neck. A protective sheath similar to sheath 501 shown in FIG. 5 may be used to protect tissue during placement of the fibrous elements 905, particularly in the case where the tissue engaging element is a non-directional frictional feature. After placement, a central portion 930 of the retractor engages tissue beneath the pharyngeal wall. Needles 920 may be incorporated into the fibrous elements 905 to facilitate placement.

The fibrous elements 905 are tensioned to retract the pharyngeal wall by producing tension on tissue beneath the lateral pharyngeal wall, or a tenting effect of the lateral wall if the elements are placed with a slight posterior/lateral and anterior/lateral angle during passage. Once sufficient tension is applied, and the lateral wall is suspended, the ends of the fibrous elements 905 are trimmed flush with the surface of the skin S and are allowed to retract slightly to remain in a sub-dermal position. Alternatively, the retractor elements may be passed directly laterally to exit the lateral tissue of the neck of the patient to provide direct lateral suspension of the pharyngeal wall.

Figure 10:
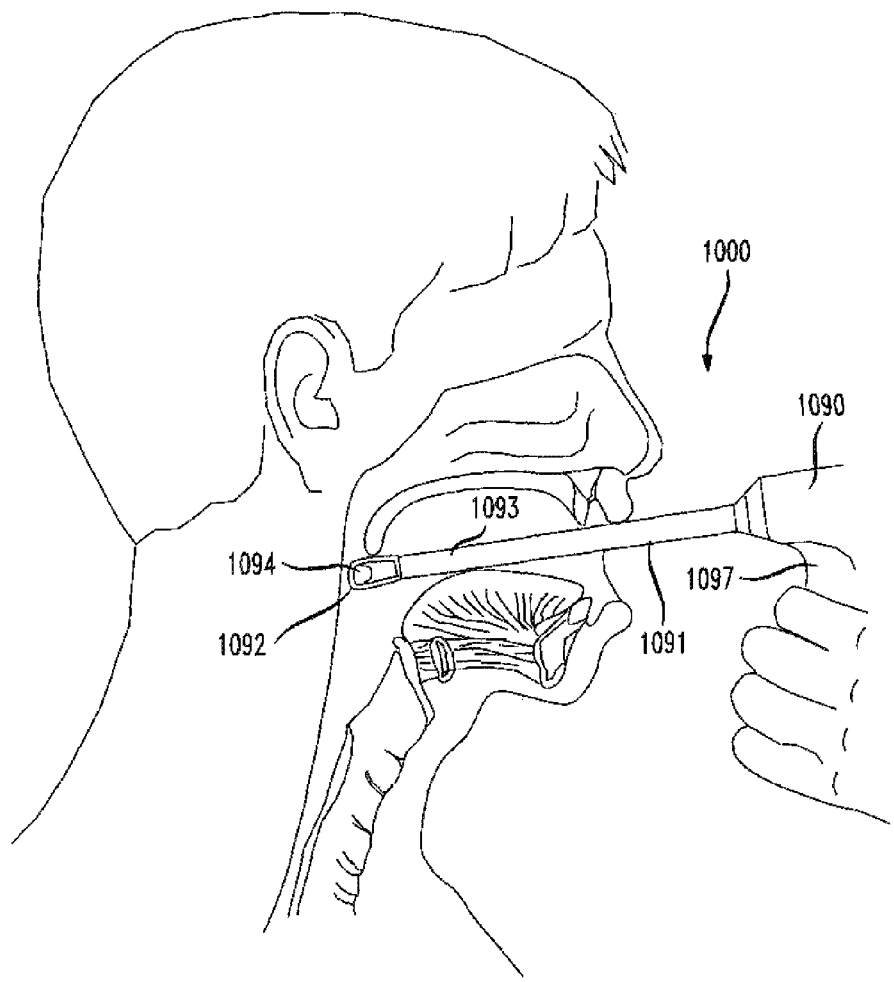
FIG. 10 is a schematic representation of a patient's head showing a pharyngeal retractor implantation method according to one embodiment of the invention.

In another method of implantation, the pharyngeal retractors described above are implanted through an oral route. In its simplest embodiment, the method of implanting the device utilizes conventional surgical instruments such as a scalpel, forceps, etc with direct visualization of the pharyngeal wall though the mouth. Alternatively, the devices can be implanted using a hand-held delivery system. FIG. 10 illustrates the approach used to deliver one of the pharyngeal retractors previously illustrated in FIGS. 6a-6f. The hand-held delivery system 1000 comprises a hand-piece 1090, a shaft 1091 extending therefrom, and a housing 1092 on the distal end 1093 of the shaft 1091. The housing is capable of holding at least one of the pharyngeal retractors 1094. The pharyngeal retractors are held in the housing in a constrained configuration.

The pharyngeal retractors are advanced out of the delivery system by a deployment means actuated by a lever 1097 on the hand-piece 1090. As the pharyngeal retractors are advanced out of the housing, they are deployed through a previously made incision in either the posterior or the lateral pharyngeal wall. Alternatively, the distal-most portion of the delivery system may have a sharpened edge to facilitate penetration of the pharyngeal wall during deployment of the refractor 1094. The retractors can then be set beneath the pharyngeal walls to provide constant refraction of the airway.

Figure 11A:
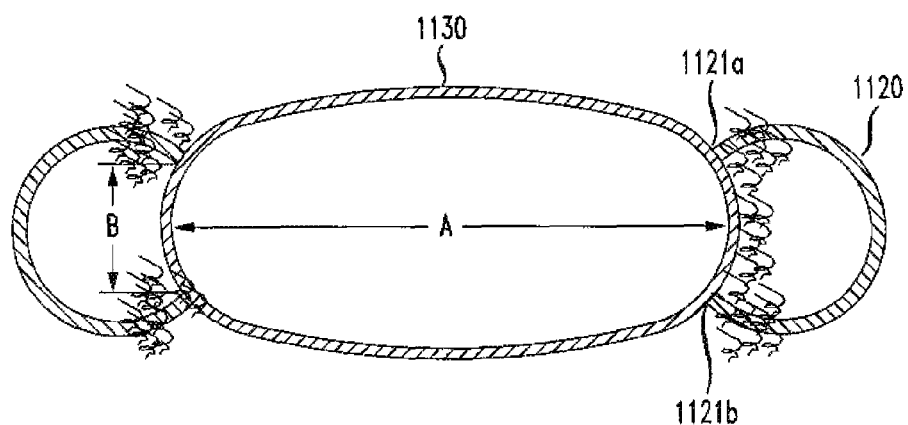
FIG. 11a is a schematic cross-sectional representation of a patient's upper airway showing two pharyngeal retractors during an implantation process according to one embodiment of the invention.
Figure 11B:
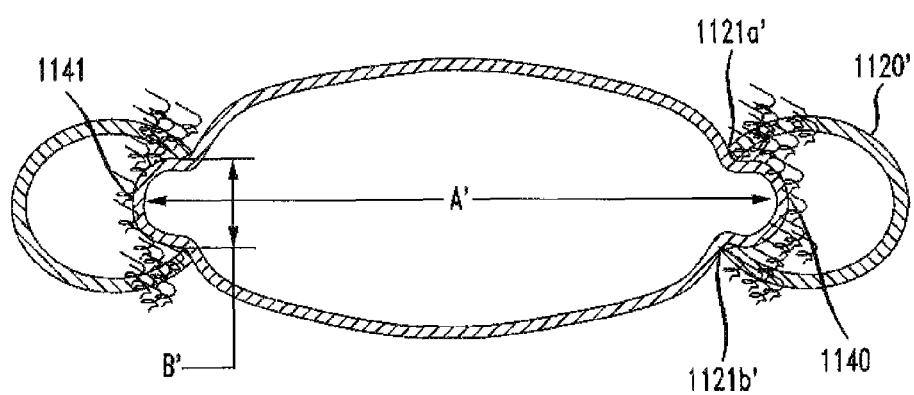
FIG. 11b is a schematic cross-sectional representation of a patient's upper airway showing the two pharyngeal retractors of FIG. 11a after implantation.

FIGS. 11a and 11b illustrate the effect of implanting two of the devices of the invention to alter the shape of the pharyngeal airway. The distance between the left lateral pharyngeal surface and the right lateral surface is represented by distance A. The retractors 1120 are shown in FIG. 11a in a constrained configuration, with a distance B between the ends of each retractor which is greater than the distance between the ends of the unconstrained refractor. The retractor is maintained in the constrained configuration with the tips 1121a, 1121b spread open within a delivery cannula or hollow stylus. The implantable device is passed into the tissues beneath the pharyngeal wall within a pre-defined arc of the cannula or hollow stylus.

Upon termination of the stylus advancement, the implantable device is ejected from the cannula or stylus by a pusher that maintains the implantable device in a fixed position while the cannula/stylus is withdrawn from the penetrated tissue beneath the pharyngeal wall. Effectively, the implantable device does not move; rather, the stylus is withdrawn from around the implantable device. After deployment, the implantable device returns to its unconstrained configuration with the tips 1121a', 1121b' of the retractors 1120' contracting as shown in FIG. 11b to the distance represented as B', which is smaller than distance B.

When the implantable device is placed in position beneath the pharyngeal wall 1030, the tips 1121a, 1121b of the device engage the pharyngeal wall so that the wall changes shape as the distance B between the tips changes. For example, the tips may engage the pharyngeal wall by pinching a portion of the wall between them. In another example, the tips 1121*a*, 1121*b* may have barbs, hooks, roughening or another tissue engaging feature to maintain engagement of the tips with the pharyngeal wall to exert a force on the wall.

After deployment of the two devices, the distance A between the lateral pharyngeal walls increases to A', and the shape of the airway is altered to produce two small irregular channels 1140, 1141 of decreased radius of curvature in the pharyngeal wall 1130 parallel to the axis of the airway. The geometry of the channels is sufficiently small to prevent the relaxed tongue from forming a seal with the pharyngeal wall along those locations while a patient is in a sleeping state and the musculature of the tongue relaxes. While the tongue may seal with the posterior pharyngeal wall, the lateral aspects are maintained as open channels 1140, 1141, effectively allowing air to flow past the obstruction.

Figure 12A:
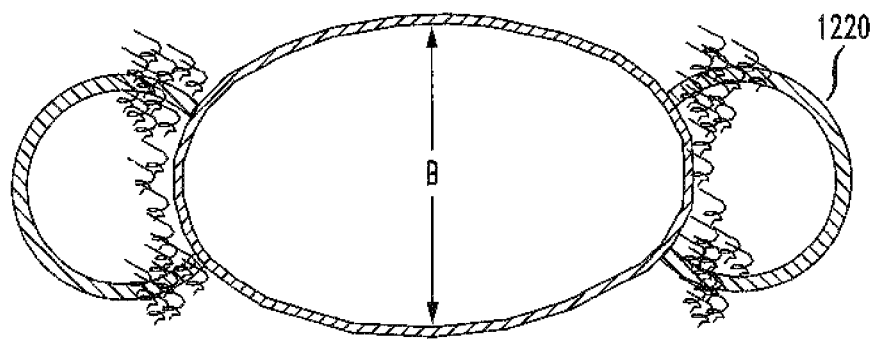
FIG. 12a is a schematic cross-sectional representation of a patient's upper airway showing two pharyngeal retractors during an implantation process according to another embodiment of the invention.
Figure 12B:
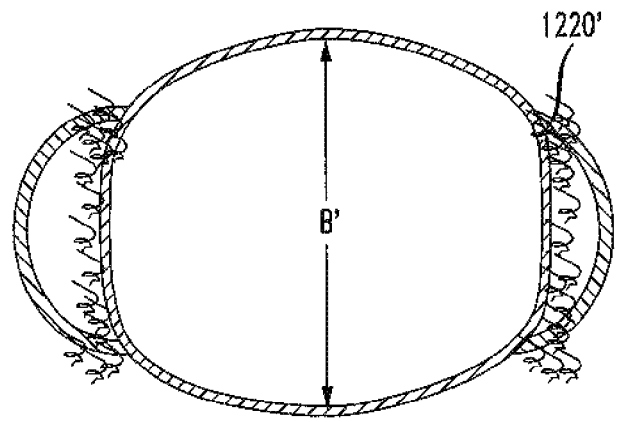
FIG. 12b is a schematic cross-sectional representation of a patient's upper airway showing the two pharyngeal retractors of FIG. 12a after implantation.

In another embodiment of the invention shown in FIGS. 12*a* and 12*b*, two implantable devices 1220 are used to produce anterior-to-posterior retraction of the pharyngeal airway to alter the shape of the airway. The distance between the anterior pharyngeal wall surface and the posterior pharyngeal wall surface is shown in FIG. 12*a* as distance B. Similar to the embodiment discussed in FIG. 11, the implantable devices are illustrated in FIG. 12 as deployed through the use of a deployment cannula or hollow stylus. The cannula or hollow stylus has a curved interior having an arch shape with a radius smaller than a radius of the implantable device in its free state. The device is essentially held in a constrained configuration within the cannula or stylus and is allowed to release during deployment. The ejection of the device from within the hollow cannula or stylus is again accomplished through the use of a pusher that maintains the device in a fixed position as the cannula is retracted.

During ejection, the radius of the implantable device increases and the distance between the tips of the device increases. Since the unconstrained devices 1220' have a distance between the ends that is greater than the distance between ends of the constrained devices, the anterior-to-posterior dimension B of the pharyngeal airway increases to B', thereby changing the shape of the airway by increasing the radius of curvature of the wall, as shown in FIG. 12*b*. In this embodiment, the base of the tongue is also partially retracted from the edges of the tongue that abut the lateral location of the pharyngeal wall, the shape of which has been altered through the use of the implantable devices.

Figure 13:
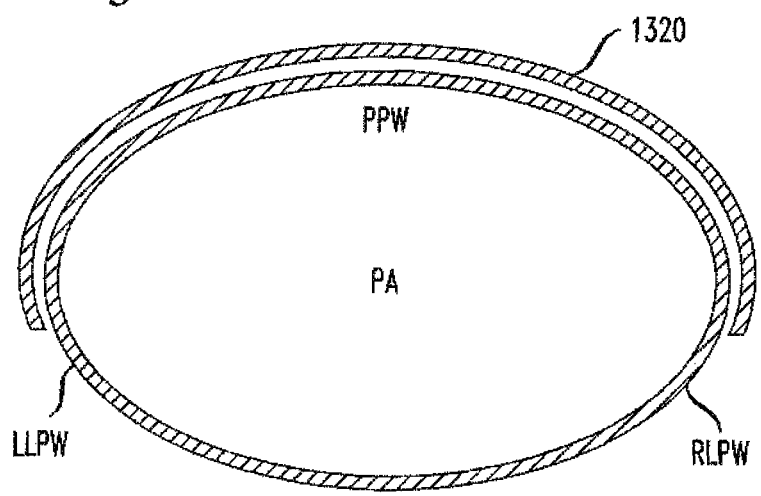
FIG. 13 is a cross-sectional representation of a patient's upper airway showing a pharyngeal retractor according to another embodiment of the invention.

While the implantable devices illustrated in FIGS. 11 and 12 are shown in the space beneath each of the lateral pharyngeal wall positions, a single device 1320 may be placed beneath the posterior pharyngeal wall (PPW) in a concentric placement to the axis of the pharynx (PA), as shown in FIG. 13. In this position, the device alters the shape of both lateral pharyngeal walls (LLPW & RLPW), thereby increasing the cross sectional area of the airway. Various length devices are feasible depending upon the severity of the pharyngeal wall collapse during sleep. In the case of pharyngeal wall collapse in the wakeful state, the implantable device may be fabricated to expand upon insertion, similar to the retractor illustrated in FIG. 12, to provide additional refraction during the awake state.

The devices, systems and surgical methods described above provide simple, minimally invasive procedures that may potentially be performed on an outpatient basis. Results of the procedures are both immediate and long-term. The implanted devices do not impact the hyoid bone or soft palate, and are therefore less likely to affect swallowing or speech. The invention furthermore uses materials with a long-term history of biocompatibility.

The foregoing Detailed Description and accompanying figures are to be understood as being in every respect illustrative and exemplary, but not restrictive, and the scope of the invention disclosed herein is not to be determined from the Description of the Invention, but rather from the Claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention.

What is claimed is:

1. A method for surgically treating obstructive sleep apnea, the method comprising the steps of:
    delivering an implantable device having first and second ends into tissue located beneath a pharyngeal wall, including introducing the implantable device orally and through the pharyngeal wall into the tissue beneath the pharyngeal wall, further including:
    positioning a distal end of a trocar proximate the pharyngeal wall, wherein the implantable device is covered by a protective sheath, the protective sheath having a trocar sleeve at one end and wherein the trocar sleeve covers the distal end of the trocar;
    inserting the distal end of the trocar at a first location in the pharyngeal wall;
    passing the implantable device through the tissue beneath the pharyngeal wall;
    further advancing the trocar to exit the pharyngeal wall through a second location; and
    removing the protective sheath from the implantable device by pulling the trocar sleeve until the sheath exits the pharyngeal wall.

2. The method of claim 1, further comprising the step of: making one or more incisions in the pharyngeal wall.

3. The method of claim 1, further comprising the step of: changing a radius of curvature of a portion of the pharyngeal wall.

4. The method of claim 1, further comprising the step of: inducing tissue ingrowth into the implantable device.

5. The method of claim 1, wherein the implantable device is a mesh.

6. The method of claim 1, wherein the trocar has a sharpened distal end.

7. A method for surgically treating obstructive sleep apnea, the method comprising steps of:
    delivering a retractor having first and second ends into tissue located beneath a pharyngeal wall, including introducing the retractor orally and through the pharyngeal wall into the tissue beneath the pharyngeal wall, further including:
    creating an a medial incision in the lateral aspect of the pharyngeal wall;
    positioning the first end of the retractor in and through the medial incision;
    positioning the second end of the retractor in and through the medial incision;
    advancing the first end of the retractor in a first lateral orientation through the tissue beneath the pharyngeal wall; and
    advancing the second end of the retractor in a second lateral orientation through the tissue beneath the pharyngeal wall;

wherein the steps of advancing the retractor's first and second ends places tension on the pharyngeal wall thereby retracting the pharyngeal wall.

8. The method of claim 7, wherein the first end of the retractor is further advanced through the skin of the neck.

9. The method of claim 8, wherein the second end of the retractor is further advanced through the skin of the neck.

10. The method of claim 8 or 9, wherein the ends of the retractor outside of the skin of the neck are trimmed.

11. The method of claim 10, where in the trimmed ends of the retractor are allowed to retract slightly to remain in a sub-dermal position.

12. The method of claim 7, wherein the retractor includes tissue engaging features.

13. The method of claim 12, wherein the tissue engaging feature is a directional frictional feature.

14. The method of claim 13, wherein the directional frictional feature is a barb.

15. The method of claim 12, wherein the retractor is a monofilament barb.

16. The method of claim 12, wherein the retractor is a braided textile structure with frictional elements encased in the braid.

17. The method of claim 12, wherein the retractor is a textile or filaments with a roughened surface.

18. The method of claim 12, wherein the retractor is a textile or filaments with a high-friction surface.

19. The method of claim 12, wherein the tissue engaging feature is a non-directional feature.

20. The method of claim 19, wherein the non-directional frictional feature is a textile.

21. The method of claim 7, wherein the retractor includes a protective sheath.

22. The method of claim 7, wherein the retractor's ends further comprise needles.

23. The method of claim 7, wherein the first end and the second end of the retractor are advanced on the same side of a line whose orientation is anterior-posterior to the pharyngeal wall and center to the lateral aspects of the pharyngeal wall.

24. The method of claim 7, wherein the first end of the retractor is advanced at least partially in a posterior orientation and second end of the retractor is advanced at least partially in an anterior orientation and wherein the first end and the second end are advanced on the same side of a line whose orientation is anterior-posterior to the pharyngeal wall and center to the lateral aspects of the pharyngeal wall.

* * * * *